(12) United States Patent
Liou et al.

(10) Patent No.: US 7,349,086 B2
(45) Date of Patent: Mar. 25, 2008

(54) SYSTEMS AND METHODS FOR OPTICAL MEASUREMENT

(75) Inventors: Joung-Wei Liou, Zhudong Town (TW); Jacky Huang, Chu-Bei (TW); Chih-Ming Ke, Hsinchu (TW); Szu-An Wu, Hsinchu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 196 days.

(21) Appl. No.: 11/322,540

(22) Filed: Dec. 30, 2005

(65) Prior Publication Data

US 2007/0153272 A1    Jul. 5, 2007

(51) Int. Cl.
  *G01J 4/00*  (2006.01)
(52) U.S. Cl. ...................... 356/364; 356/369
(58) Field of Classification Search ............. None
  See application file for complete search history.

(56) References Cited

U.S. PATENT DOCUMENTS

| 7,019,850 B2 * | 3/2006 | Finarov ............... 356/630 |
| 7,023,549 B2 * | 4/2006 | Shchegrov et al. .... 356/369 |
| 2003/0128372 A1 * | 7/2003 | Sidorowich ............ 356/630 |

* cited by examiner

*Primary Examiner*—Michael P. Stafira
(74) *Attorney, Agent, or Firm*—Thomas, Kayden, Horstemeyer & Risley

(57) ABSTRACT

A system for measuring optical properties of a sample is provided. A light source provides incident polarized light. A detector detects reflected light from the sample surface. A processor determines a first coefficient (R) of the reflected light detected by the detector, determines a second coefficient (n), extinction coefficient (k), and thickness of the film based on the measured first coefficient, and determines a first dielectric constant ($\epsilon_1$) and a second dielectric constant ($\epsilon_2$) of the film according to the second coefficient (n) and extinction coefficient (k).

22 Claims, 2 Drawing Sheets

SYSTEMS AND METHODS FOR OPTICAL MEASUREMENT

BACKGROUND

The present invention relates to semiconductor manufacturing, and more particularly, to systems and methods of optical measurement implemented in a semiconductor manufacturing environment.

With the use of multilayer thin films and increasing complexity of device fabrication, spectroscopic ellipsometry (SE) has emerged as the technique of choice for monitoring thin-film processes through different stages of integrated circuit (IC) device fabrication. SE monitors and characterizes fabrication processes by measuring the optical properties of materials through the analysis of reflected, polarized light.

Recently, anisotropic materials, such as amorphous carbon, have been widely used in IC fabrication. Conventional spectroscopic ellipsometry, however, cannot correctly characterize amorphous carbon film.

Hence, systems and methods that address problems arising from the existing technology are desirable.

SUMMARY

A system for measuring optical properties of a sample is provided. The system comprises a light source, a detector, and a processor. The light source provides incident polarized light. The detector detects reflected light from the sample surface. The processor determines a reflection coefficient (R) of the reflected light detected by the detector, determines a refractive index (n), extinction coefficient (k), and thickness of the film based on the measured reflection coefficient, and determines a first dielectric constant ($\in_1$) and a second dielectric constant ($\in_2$) of the film according to the refractive index (n) and extinction coefficient (k).

Also disclosed is a method of optical measurement. A film is provided. A reflection coefficient (R) of an incident beam reflected by the film is measured. A refractive index (n), extinction coefficient (k), and thickness of the film are determined based on the measured reflection coefficient. A first dielectric constant ($\in_1$) and a second dielectric constant ($\in_2$) of the film are determined according to the refractive index (n) and extinction coefficient (k).

The above-mentioned method may take the form of program code embodied in a tangible media. When the program code is loaded into and executed by a machine, the machine becomes an apparatus for practicing the invention.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION

The invention will now be described with reference to FIGS. 1 and 2, which generally relate to systems and methods of optical measurement.

In the following detailed description, reference is made to the accompanying drawings which form a part hereof, and in which is shown by way of illustration of specific embodiments. These embodiments are described in sufficient detail to enable those skilled in the art to practice the invention, and it is to be understood that other embodiments may be utilized and that structural, logical and electrical changes may be made without departing from the spirit and scope of the present invention. The following detailed description is, therefore, not to be taken in a limiting sense. The leading digit(s) of reference numbers appearing in the figures corresponds to the figure number, with the exception that the same reference number is used throughout to refer to an identical component which appears in multiple figures.

Figure 1:
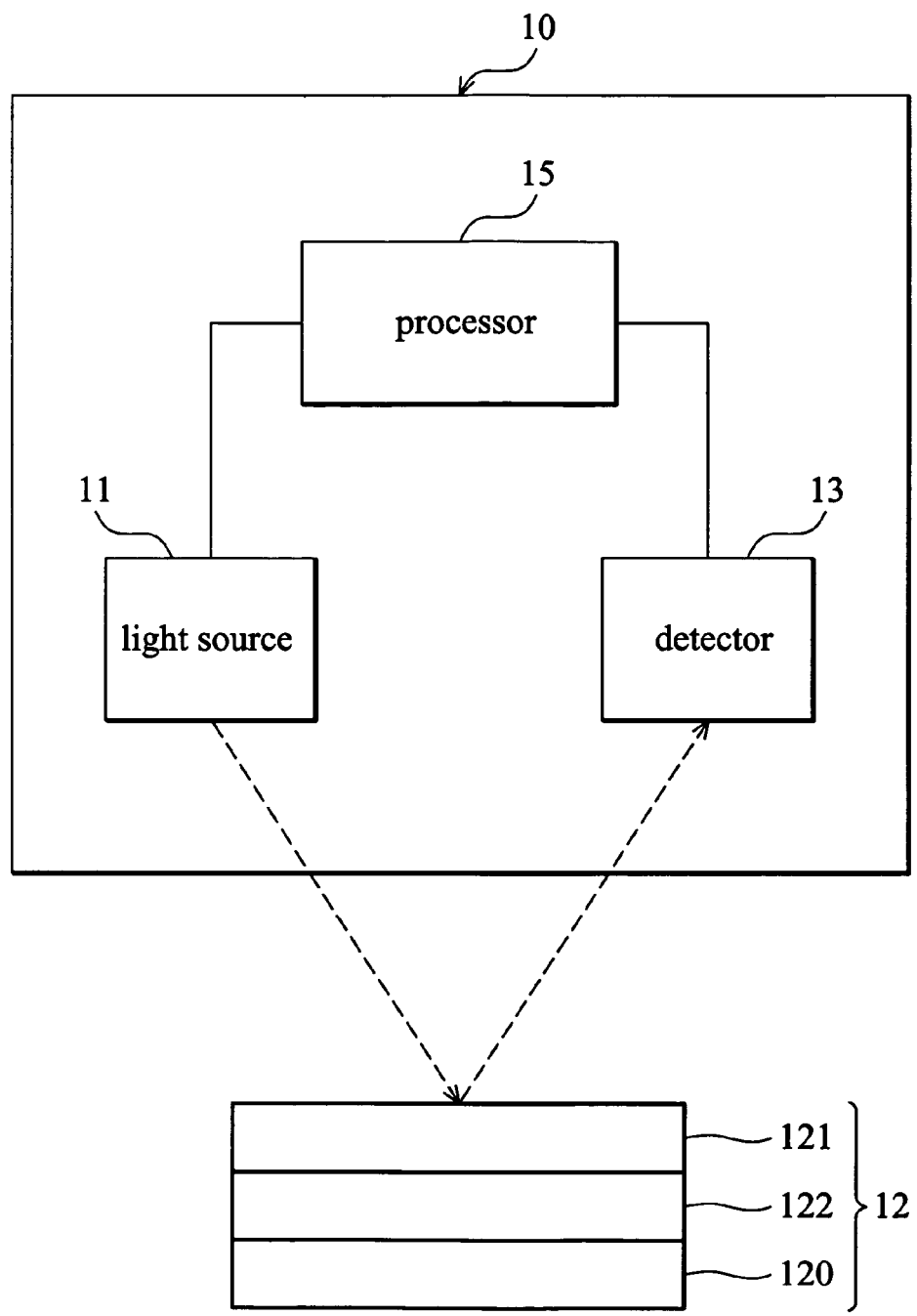
FIG. 1 illustrates an embodiment of a system for measuring optical properties of a sample.

FIG. 1 illustrates an embodiment of a system for measuring optical properties of a sample, such as a thin film. A system 10 is an optical measuring system for measuring optical properties of a sample 12. System 10 can be a spectrometer or ellipsometer using multiple angles and wavelengths. System 10 comprises a light source 11, a detector 13, and a processor 15. System 10 can be an ellipsometer or a spectrometer using incident beam of different wavelengths and/or incident angles;

Light source 11 provides incident polarized light comprising a parallel component (p) and perpendicular component (s).

The detector 13 detects reflected light from the sample surface. Reflected light corresponding to the p and s components of the incident beams is detected, respectively.

The processor 15 first determines a reflection coefficient (R) of the reflected light detected by the detector. Processor 15 then determines a refractive index (n), extinction coefficient (k), and thickness of the film based on the measured reflection coefficient, and determines a first dielectric constant ($\in_1$) and a second dielectric constant ($\in_2$) of the film according to the refractive index (n) and extinction coefficient (k). Processor 15 determines reflection coefficients corresponding to the p and s components of the incident beam, respectively.

For example, sample 12 is a multilayer film comprising a first layer 121, a second layer 122, and a substrate 120. Processor 15 determines the refractive index (n), extinction coefficient (k), and thickness of the film according to the following formula:

$$R_{(p)} = \frac{(r_{01(p)}^2 + r_{12(p)}^2 + 2r_{01(p)}r_{12(p)}\cos 2\alpha_{(p)})}{(1 + r_{01(p)}r_{12(p)})^2 + 2r_{01(p)}r_{12(p)}\cos 2\alpha_{(p)}}, \quad \text{(formula 1)}$$

$$R_{(s)} = \frac{(r_{01(s)}^2 + r_{12(s)}^2 + 2r_{01(s)}r_{12(s)}\cos 2\alpha_{(s)})}{(1 + r_{01(s)}r_{12(s)})^2 + 2r_{01(s)}r_{12(s)}\cos 2\alpha_{(s)}}, \quad \text{(formula 2)}$$

in which, $R_{(p)}$ and $R_{(s)}$ are reflection coefficients of the p and s components, respectively; $r_{01(p)}$ and $r_{01(s)}$ are the Fresnel coefficients of the p and s components from a medium (0) to the first layer, respectively; $r_{12(p)}$ and $r_{12(s)}$ are the Fresnel coefficients of the p and s components from the first layer (1) to the second layer (2), respectively; and $\alpha_{(p)}$ and $\alpha_{(s)}$ are the phase change in p and s components of the incident beam wave as they move from the top of the film to the bottom of the film, respectively.

$\alpha_{(p)}$ of formulae (1) and (2) is defined according to formula (3):

$$\alpha_{(p)} = 2\pi d/\lambda (Nx/Nz)\sqrt{Nz^2 - \sin^2\theta}, \quad \text{(formula 3)}$$

in which, d is thickness of the film, λ is wavelength of the polarized light, $N_x$ is the refractive index in x direction, $N_y$ is refractive index in y direction, $N_z$ is refractive index in z direction, and θ is incident angle with respect to normal direction.

$\alpha_{(s)}$ of the formulae (1) and (2) is defined according to formula (4):

$$\alpha_{(s)} = 2\pi d/\lambda \sqrt{Nx^2 - \sin^2\theta} \qquad \text{(formula 4)}$$

In formula (4), d is thickness of the film, λ is wavelength of the polarized light, $N_x$ is the refractive index in x direction, and θ is incident angle with respect to normal direction.

After refractive index (n) and extinction coefficient (k) of sample 12 are determined, processor 15 determines the first dielectric constant ($\in_1$) and second dielectric constant ($\in_2$) according to formulae (5) and (6):

$$n = \sqrt{\frac{(\varepsilon_1^2 + \varepsilon_2^2)^{\frac{1}{2}}}{2} + \varepsilon_1} \qquad \text{(formula 5)}$$

$$k = \sqrt{\frac{(\varepsilon_1^2 + \varepsilon_2^2)^{\frac{1}{2}}}{2} - \varepsilon_1} \qquad \text{(formula 6)}$$

The first dielectric constant ($\in_1$) and second dielectric constant ($\in_2$) specify optical properties of the sample, and can be used for further analysis. Additionally, the first dielectric constant ($\in_1$) specifies a real part of anisotropy ratio of sample 12, and the second dielectric constant ($\in_2$) specifies an imaginary part of anisotropy ratio of sample 12.

Figure 2:
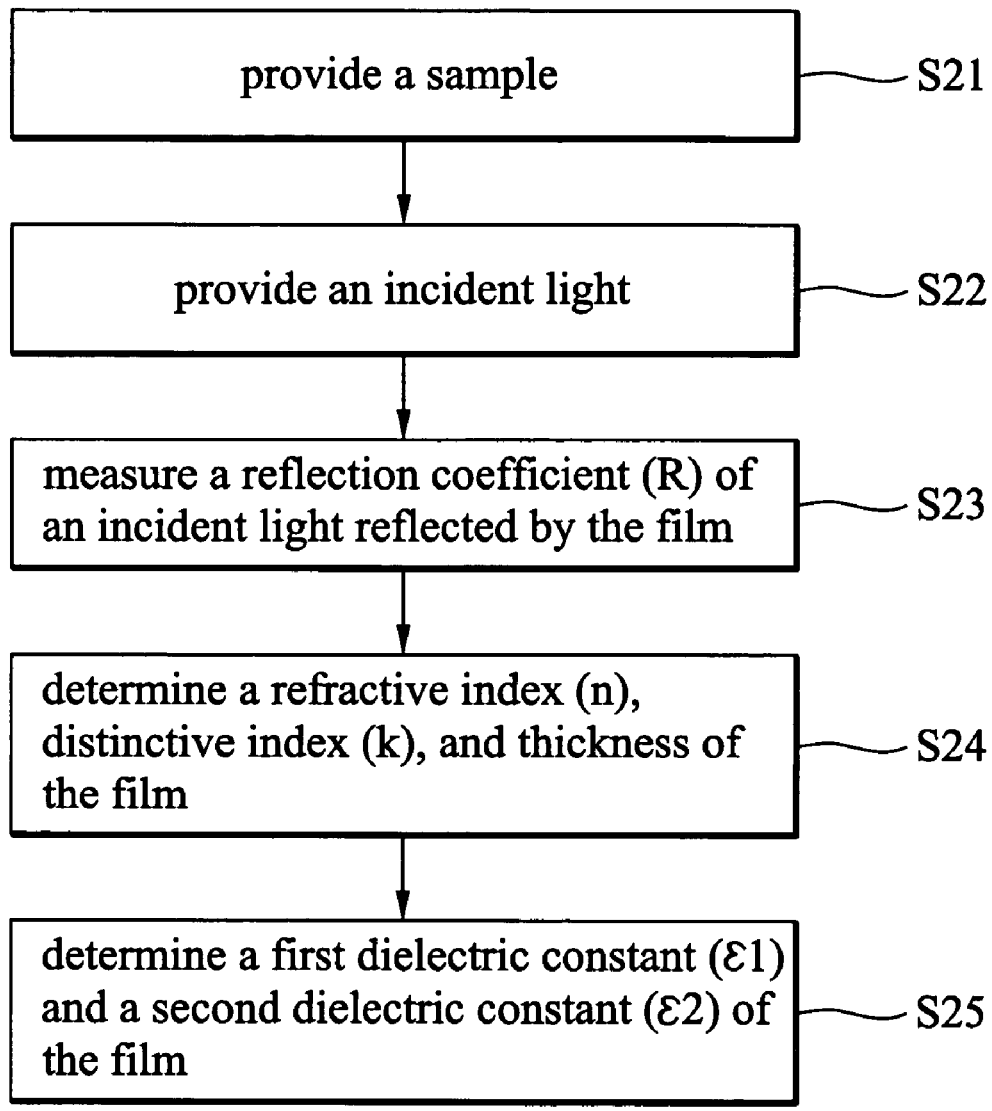
FIG. 2 is a flowchart of an embodiment of a method of optical measurement.

FIG. 2 is a flowchart of an embodiment of a method of optical measurement. In step S21, a sample, such as a film, is provided. In step S22, an incident beam is provided to characterize the sample. The incident beam comprises a parallel component (component p) and perpendicular component (component s). The reflection coefficients corresponding to the p and s components of the incident beam are measured respectively.

In step S23, reflection coefficient (R) of an incident beam reflected by the film is measured.

In step S25, refractive index (n), extinction coefficient (k), and thickness of the film are determined based on the measured reflection coefficient.

For example, if the film comprises a first layer (1) and a second layer (2), the refractive index (n), extinction coefficient (k), and thickness of the film are determined according to formulae (1) and (2):

$$R_{(p)} = \frac{(r_{01(p)}^2 + r_{12(p)}^2 + 2r_{01(p)}r_{12(p)}\cos 2\alpha_{(p)})}{(1 + r_{01(p)}r_{12(p)})^2 + 2r_{01(p)}r_{12(p)}\cos 2\alpha_{(p)}}, \qquad \text{(formula 1)}$$

$$R_{(s)} = \frac{(r_{01(s)}^2 + r_{12(s)}^2 + 2r_{01(s)}r_{12(s)}\cos 2\alpha_{(s)})}{(1 + r_{01(s)}r_{12(s)})^2 + 2r_{01(s)}r_{12(s)}\cos 2\alpha_{(s)}}, \qquad \text{(formula 2)}$$

in which, $R_{(p)}$ and $R_{(s)}$ are reflection coefficients of the p and s components, respectively; $r_{01(p)}$ and $r_{01(s)}$ are the Fresnel coefficients of the p and s components from a medium (0) to the first layer, respectively; $r_{12(p)}$ and $r_{12(s)}$ are the Fresnel coefficients of the p and s components from the first layer (1) to the second layer (2), respectively; and $\alpha_{(p)}$ and $\alpha_{(s)}$ are the phase change in p and s components of the incident beam wave as they move from the top of the film to the bottom of the film, respectively.

$\alpha_{(p)}$ of formulae (1) and (2) is defined according to formula (3):

$$\alpha_{(p)} = 2\pi d/\lambda (Nx/Nz)\sqrt{Nz^2 - \sin^2\theta}, \qquad \text{(formula 3)}$$

in which, d is thickness of the film, λ is wavelength of the polarized light, $N_x$ is the refractive index in x direction, $N_y$ is refractive index in y direction, $N_z$ is refractive index in z direction, and θ is incident angle with respect to normal direction.

$\alpha_{(s)}$ of formulae (1) and (2) is defined according to formula (4):

$$\alpha_{(s)} = 2\pi d/\lambda \sqrt{Nx^2 - \sin^2\theta} \qquad \text{(formula 4)}$$

in which, d is thickness of the film, λ is wavelength of the polarized light, $N_x$ is the refractive index in x direction, and θ is incident angle with respect to normal direction.

In step S27, a first dielectric constant ($\in_1$) and a second dielectric constant ($\in_2$) of the film are determined according to the refractive index (n) and extinction coefficient (k).

After refractive index (n) and extinction coefficient (k) of sample 12 are determined, the first dielectric constant ($\in_1$) and second dielectric constant ($\in_2$) are determined according to formulae (5) and (6):

$$n = \sqrt{\frac{(\varepsilon_1^2 + \varepsilon_2^2)^{\frac{1}{2}}}{2} + \varepsilon_1} \qquad \text{(formula 5)}$$

$$k = \sqrt{\frac{(\varepsilon_1^2 + \varepsilon_2^2)^{\frac{1}{2}}}{2} - \varepsilon_1} \qquad \text{(formula 6)}$$

The first dielectric constant ($\in_1$) and second dielectric constant ($\in_2$) specify optical properties of the sample, and can be used for further analysis. Additionally, the first dielectric constant ($\in_1$) specifies a real part of anisotropy ratio of sample 12, and the second dielectric constant ($\in_2$) specifies an imaginary part of anisotropy ratio of sample 12.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of optical measurement, comprising:
   providing a film;
   providing an incident beam;
   measuring a first coefficient (R) of the incident beam reflected by the film;
   determining a second coefficient (n), third coefficient (k), and thickness of the film based on the measured first coefficient; and
   determining a first dielectric constant ($\in_1$) and a second dielectric constant ($\in_2$) of the film according to the second coefficient (n) and third coefficient (k).

2. The method of claim 1, wherein the incident beam comprises a parallel component (p) and perpendicular component (s).

3. The method of claim 2, wherein the first coefficients corresponding to the p and s components of the incident beam are measured respectively.

4. The method of claim 2, wherein the film comprises a first layer (1) and a second layer (2), and the second coefficient (n), third coefficient (k), and thickness of the film are determined according to the following formula:

$$R_{(p)} = \frac{(r_{01(p)}^2 + r_{12(p)}^2 + 2r_{01(p)}r_{12(P)}\cos 2\alpha_{(p)})}{(1 + r_{01(P)}r_{12(P)})^2 + 2r_{01(P)}r_{12(P)}\cos 2\alpha_{(p)}},$$

$$R_{(s)} = \frac{(r_{01(s)}^2 + r_{12(s)}^2 + 2r_{01(s)}r_{12(s)}\cos 2\alpha_{(s)})}{(1 + r_{01(s)}r_{12(s)})^2 + 2r_{01(s)}r_{12(s)}\cos 2\alpha_{(s)}}$$

wherein the $R_{(p)}$ and $R_{(s)}$ are first coefficients of the p and s components; $r_{01(p)}$ and $r_{01(s)}$ are the Fresnel coefficients of the p and s components from a medium (0) to the first layer; $r_{12(p)}$ and $r_{12(s)}$ are the Fresnel coefficients of the p and s components from the first layer (1) to the second layer (2); and $\alpha_{(p)}$ and $\alpha_{(s)}$ are the phase change in p and s components of the incident beam wave as they move from the top of the film to the bottom of the film.

5. The method of claim 4, wherein $\alpha_{(p)}$ is determined by the following formula:

$$\alpha_{(p)} = 2\pi d/\lambda (Nx/Nz)\sqrt{Nz^2 - \sin^2\theta},$$

wherein d is thickness of the film, $\lambda$ is wavelength of the polarized light, $N_x$ is the second coefficient in x direction, $N_y$ is second coefficient in y direction, $N_z$ is second coefficient in z direction, and $\theta$ is incident angle with respect to normal direction.

6. The method of claim 4, wherein $\alpha_{(s)}$ is determined by the the following formula:

$$\alpha_{(s)} = 2\pi d/\lambda \sqrt{Nx^2 - \sin^2\theta},$$

wherein d is thickness of the film, $\lambda$ is wavelength of the polarized light, $N_x$ is the second coefficient in x direction, and $\theta$ is incident angle with respect to normal direction.

7. The method of claim 1, wherein the first coefficient is measured by an ellipsometer using incident beam of different wavelengths.

8. The method of claim 1, wherein the first coefficient is measured by an ellipsometer using incident beam of different wavelengths.

9. The method of claim 1, wherein the first coefficient is measured by a spectrometer using incident beam of different incident angles.

10. The method of claim 1, wherein the first coefficient is measured by a spectrometer using incident beam of different wavelengths.

11. The method of claim 1, wherein the first dielectric constant ($\in_1$) and second dielectric constant ($\in_2$) are determined according to the following formula:

$$n = \sqrt{\frac{(\varepsilon_1^2 + \varepsilon_2^2)^{\frac{1}{2}}}{2} + \varepsilon_1};$$

$$k = \sqrt{\frac{(\varepsilon_1^2 + \varepsilon_2^2)^{\frac{1}{2}}}{2} - \varepsilon_1}.$$

12. A system for measuring optical properties of a sample, comprising:
 a light source providing incident polarized light;
 a detector for detecting reflected light from the sample surface; and
 a processor determining a first coefficient (R) of the reflected light detected by the detector, determining a second coefficient (n), third coefficient (k), and thickness of the film based on the measured first coefficient, and determining a first dielectric constant ($\in_1$) and a second dielectric constant ($\in_2$) of the film according to the second coefficient (n) and third coefficient (k).

13. The system of claim 1, wherein the light source provides an incident beam comprising a parallel component (p) and perpendicular component (s).

14. The system of claim 13, wherein the processor determines first coefficients corresponding to the p and s components of the incident beam, respectively.

15. The system of claim 13, wherein the sample is a multilayer film comprising a first layer (1) and a second layer (2), and the processor determines the second coefficient (n), third coefficient (k), and thickness of the film according to the following formula:

$$R_{(p)} = \frac{(r_{01(p)}^2 + r_{12(P)}^2 + 2r_{01(p)}r_{12(P)}\cos 2\alpha_{(p)})}{(1 + r_{01(P)}r_{12(P)})^2 + 2r_{01(P)}r_{12(P)}\cos 2\alpha_{(p)}},$$

$$R_{(s)} = \frac{(r_{01(s)}^2 + r_{12(s)}^2 + 2r_{01(s)}r_{12(s)}\cos 2\alpha_{(s)})}{(1 + r_{01(s)}r_{12(s)})^2 + 2r_{01(s)}r_{12(s)}\cos 2\alpha_{(s)}}$$

wherein the $R_{(p)}$ and $R_{(s)}$ are first coefficients of the p and s components; $r_{01(p)}$ and $r_{01(s)}$ are the Fresnel coefficients of the p and s components from a medium (0) to the first layer; $r_{12(p)}$ and $r_{12(s)}$ are the Fresnel coefficients of the p and s components from the first layer (1) to the second layer (2); and $\alpha_{(p)}$ and $\alpha_{(s)}$ are the phase change in p and s components of the incident beam wave as they move from the top of the film to the bottom of the film.

16. The system of claim 15, wherein the processor determines $\alpha_{(p)}$ based on the following formula:

$$\alpha_{(p)} = 2\pi d/\lambda (Nx/Nz)\sqrt{Nz^2 - \sin^2\theta},$$

wherein d is thickness of the film, $\lambda$ is wavelength of the polarized light, $N_x$ is the second coefficient in x direction, $N_y$ is second coefficient in y direction, $N_z$ is second coefficient in z direction, and $\theta$ is incident angle with respect to normal direction.

17. The system of claim 15, wherein $\alpha_{(s)}$ is determined by the following formula:

$$\alpha_{(s)} = 2\pi d/\lambda \sqrt{Nx^2 - \sin^2\theta},$$

wherein d is thickness of the film, $\lambda$ is wavelength of the polarized light, $N_x$ is the second coefficient in x direction, and $\theta$ is incident angle with respect to normal direction.

18. The system of claim 12, wherein the system implements an ellipsometer using incident beam of different wavelengths.

19. The system of claim 12, wherein the system implements an ellipsometer using incident beam of different incident angles.

20. The system of claim 12, wherein the system implements a spectrometer using incident beam of different incident angles.

21. The system of claim 12, wherein the system implements a spectrometer using incident beam of different wavelengths.

22. The system of claim 12, wherein the processor determines the first dielectric constant ($\varepsilon_1$) and second dielectric constant ($\varepsilon_2$) according to the following formulae:

$$n = \sqrt{\frac{(\varepsilon_1^2 + \varepsilon_2^2)^{\frac{1}{2}}}{2} + \varepsilon_1} \; ;$$

$$k = \sqrt{\frac{(\varepsilon_1^2 + \varepsilon_2^2)^{\frac{1}{2}}}{2} - \varepsilon_1} \; .$$

wherein the dielectric constant comprises an ordinary parts ($\square_o$) dielectric function and an extra-ordinary parts ($\square_e$) dielectric function, wherein the dielectric function is a complex number, including a real part and an imaginary part.

* * * * *